(12) United States Patent
Spencer et al.

(10) Patent No.: US 11,553,889 B2
(45) Date of Patent: Jan. 17, 2023

(54) DEVICES, SYSTEMS, AND METHODS FOR IMPROVED ACCURACY MODEL OF VESSEL ANATOMY

(71) Applicant: PHILIPS IMAGE GUIDED THERAPY CORPORATION, San Diego, CA (US)

(72) Inventors: Jason Spencer, San Diego, CA (US); Joseph Hoffman, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 361 days.

(21) Appl. No.: 16/748,928

(22) Filed: Jan. 22, 2020

(65) Prior Publication Data

US 2020/0155107 A1 May 21, 2020

Related U.S. Application Data

(63) Continuation of application No. 14/798,218, filed on Jul. 13, 2015, now Pat. No. 10,542,954.
(Continued)

(51) Int. Cl.
*A61B 6/00* (2006.01)
*A61B 8/12* (2006.01)
(Continued)

(52) U.S. Cl.
CPC .............. *A61B 6/5247* (2013.01); *A61B 6/12* (2013.01); *A61B 6/485* (2013.01); *A61B 6/487* (2013.01);
(Continued)

(58) Field of Classification Search
CPC ......... A61B 6/5247; A61B 6/12; A61B 6/485; A61B 6/487; A61B 6/504; A61B 8/0841;
(Continued)

(56) References Cited

U.S. PATENT DOCUMENTS 5,054,492 A 10/1991 Scribner
5,453,575 A 9/1995 O'Donnell
(Continued)

FOREIGN PATENT DOCUMENTS

WO 2014084382 A1 6/2014

OTHER PUBLICATIONS

Iihnatsenka et al Ultrasound: Basic Understanding and learning the language 2010, International Journal of Sholder Surgery, p. 3.

*Primary Examiner* — Sanjay Cattungal (57) ABSTRACT

Devices, systems, and methods of imaging a blood vessel are provided. For example, the method can include obtaining fluoroscopic image data of a region of interest in a blood vessel using an x-ray source; obtaining intravascular ultrasound (IVUS) data at a plurality of positions across the region of interest using an IVUS component disposed on an intravascular device; processing the fluoroscopic image data and IVUS data, including: determining, using the fluoroscopic image data, a position of the intravascular device with respect to the x-ray source at each of the plurality of positions across the region of interest; co-registering the fluoroscopic image data and the IVUS image data; and generating, a model of the region of interest including position information of a border of a lumen of the blood vessel at each of the plurality of locations; and outputting a visual representation of the model of the region of interest.

30 Claims, 6 Drawing Sheets

Related U.S. Application Data (60) Provisional application No. 62/024,339, filed on Jul. 14, 2014.

(51) Int. Cl.

| | | |
|---|---|---|
| *A61B 8/08* | (2006.01) | |
| *A61B 6/12* | (2006.01) | |
| *G01S 15/89* | (2006.01) | |
| *A61B 8/00* | (2006.01) | |
| *A61B 90/00* | (2016.01) | |
| *A61B 8/06* | (2006.01) | |
| *G01S 7/52* | (2006.01) | |

(52) U.S. Cl.
CPC ............ *A61B 6/504* (2013.01); *A61B 8/0841* (2013.01); *A61B 8/12* (2013.01); *A61B 8/4263* (2013.01); *A61B 8/5261* (2013.01); *A61B 90/39* (2016.02); *G01S 15/899* (2013.01); *G01S 15/8952* (2013.01); *A61B 8/06* (2013.01); *A61B 8/0891* (2013.01); *G01S 7/52036* (2013.01); *G01S 15/894* (2013.01); *G01S 15/8922* (2013.01); *G01S 15/8981* (2013.01)

(58) Field of Classification Search
CPC ....... A61B 8/12; A61B 8/4263; A61B 8/5261; A61B 90/39; A61B 8/06; A61B 8/0891; A61B 2090/364; A61B 2090/3966; G01S 15/8952; G01S 15/899; G01S 7/52036; G01S 15/8922; G01S 15/894; G01S 15/8981

See application file for complete search history.

(56) References Cited

U.S. PATENT DOCUMENTS

| | | | |
|---|---|---|---|
| 6,010,511 | A | 1/2000 | Murphy |
| 7,846,101 | B2 | 12/2010 | Eberle |
| 2004/0116813 | A1 | 6/2004 | Selzer |
| 2006/0241465 | A1 | 10/2006 | Huennekens |
| 2007/0038061 | A1* | 2/2007 | Huennekens .......... A61B 6/504 600/407 |
| 2008/0004530 | A1* | 1/2008 | Feldman ................ A61B 6/504 600/467 |
| 2011/0087104 | A1* | 4/2011 | Moore ................ G01S 7/52071 600/447 |
| 2011/0160586 | A1* | 6/2011 | Li ........................ G01S 15/8952 600/443 |
| 2012/0004537 | A1* | 1/2012 | Tolkowsky .............. A61B 8/12 600/424 |
| 2013/0030295 | A1 | 1/2013 | Huennekens |
| 2014/0056099 | A1 | 2/2014 | Hancock |
| 2014/0100453 | A1 | 4/2014 | Kemp |
| 2014/0180108 | A1* | 6/2014 | Rice .................... A61B 8/4461 600/445 |
| 2014/0257087 | A1 | 9/2014 | Elbasiony |
| 2014/0276065 | A1* | 9/2014 | He ....................... A61B 8/0891 600/445 |
| 2015/0066818 | A1 | 3/2015 | Choi |
| 2016/0066881 | A1* | 3/2016 | Li ............................ A61B 8/12 600/443 |

\* cited by examiner

DEVICES, SYSTEMS, AND METHODS FOR IMPROVED ACCURACY MODEL OF VESSEL ANATOMY

CROSS REFERENCE TO RELATED APPLICATIONS

The present application is a continuation of U.S. patent application Ser. No. 14/798,218, filed Jul. 13, 2015, now U.S. Pat. No. 10,542,954, which claims priority to and the benefit of the U.S. Provisional Patent Application No. 62/024,339, filed Jul. 14, 2014, both of which are hereby incorporated by reference in their entirety.

TECHNICAL FIELD

The present disclosure relates generally to intravascular imaging and, in particular, to generating a model of vessel anatomy including anatomical and flow data. For example, some embodiments of the present disclosure provide a hybrid imaging system particularly suited for imaging a human blood vessel including, for example, angiographic/fluoroscopic imaging, intravascular ultrasound (IVUS) imaging, and/or optical coherence tomography (OCT) imaging.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound scanner assembly that includes an array of ultrasound transducers distributed around the circumference of the device connected to a set of transducer control circuits. The transducer control circuits select individual transducers or a combination of transducers for transmitting an ultrasound pulse and for receiving the echo signal. By stepping through a sequence of transmitter-receiver pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

IVUS imaging can be utilized before, during, and/or after a percutaneous coronary intervention (PCI). For example, IVUS imaging can be used for diagnosis and treatment planning to determine an appropriate diameter and length for a stent to be positioned within an occluded blood vessel. For example, after stent deployment, IVUS imaging can be used to determine if the stent is properly placed within the vessel. IVUS imaging can provide information about the vessel lumen and borders, whether the stent is well apposed to the vessel lumen, and other information for diagnosis and/or post-treatment assessment. While conventional IVUS systems provide border and lumen information, it is generally not accurate enough to automatically make treatment and a post-treatment assessment decisions. Thus, conventional IVUS imaging systems generally require human image interpretation to determine a proper diameter and length for the stent and whether the stent is well apposed to the vessel lumen.

Thus, there remains a need for intravascular ultrasound imaging system that provides a high accuracy model of vessel anatomy.

SUMMARY

Embodiments of the present disclosure provide an improved imaging system for generating model of vessel anatomy in which various components within the vessel tissue are accurately distinguished from each other and blood is accurately distinguished from tissue. The imaging system can utilize IVUS data including ultrasound emissions with different frequencies to distinguish among the various components within the vessel and ultrasound emissions separated in time to distinguish the blood from the tissue. The IVUS data can be acquired using an IVUS component including orientation marker visible in angiographic/fluoroscopic image data. The imaging system can thus utilize angiographic/fluoroscopic image data in conjunction with IVUS data to generate an improved accuracy model of vessel anatomy.

In an exemplary aspect, the present disclosure is directed to a method of imaging a blood vessel. The method includes obtaining fluoroscopic image data of a region of interest in a blood vessel using an x-ray source, the region of interest including an obstruction limiting blood flow through the blood vessel; obtaining intravascular ultrasound (IVUS) data at a plurality of positions across the region of interest using an IVUS component disposed on an intravascular device, wherein the IVUS data at each of the plurality of positions includes a plurality of components corresponding to different frequencies of ultrasound emissions, wherein successive ultrasound emissions respectively associated with each of the different frequencies are separated in time; processing the fluoroscopic image data and IVUS data, including: determining, using the fluoroscopic image data, a position of the intravascular device with respect to the x-ray source at each of the plurality of positions across the region of interest; co-registering the fluoroscopic image data and the IVUS image data; and generating, using the determined position of the intravascular device and the co-registered fluoroscopic image data and the IVUS image data, a model of the region of interest including position information of a border of a lumen of the blood vessel at each of the plurality of locations; and outputting a visual representation of the model of the region of interest.

In an exemplary aspect, the present disclosure is directed to a system. The system includes an intravascular device including an intravascular ultrasound (IVUS) component configured to acquire IVUS data at a plurality of positions across a region of interest in a blood vessel, the region of interest including an obstruction limiting blood flow through the blood vessel; a computing system in communication with the intravascular device and configured to: receive IVUS data from the intravascular device during a manual or automated pullback of the intravascular device across the obstruction, wherein the IVUS data at each of the plurality of positions includes a plurality of components corresponding to different frequencies of ultrasound emissions, wherein successive ultrasound emissions respectively associated with each of the different frequencies are separated in time; receive fluoroscopic image data of the region of interest, the fluoroscopic image data being acquired using an x-ray source simultaneously as IVUS data is being acquired; process the fluoroscopic image data and IVUS data, including: determining, using the fluoroscopic image data, a position of the intravascular device with respect to the x-ray source at each of the plurality of positions across the region of interest; co-registering the fluoroscopic image data and the IVUS image data; and generating, using the determined position of the intravascular device and the co-registered fluoroscopic image data and the IVUS image data, a model of the region of interest including position information of a border of a lumen of the blood vessel at each of the plurality of locations; and output a visual representation of the model of the region of interest.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while one or more features are described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure provides devices, systems, and methods of ultrasound imaging with improved accuracy. The algorithms described herein include the synthesis of multi-frequency/multi-gain value IVUS data over extended length pullback, as well as fluoroscopic image data to generate a high accuracy anatomical model of the vessel. In one or more aspects, the system can include an orientation-marked catheter having transducer element(s) capable of operating at multiple frequencies at each A-scan. A computing device can include filtering hardware and a video capture card. The multi-frequency IVUS data and filtering hardware, as well as information from fluoroscopic video captures of the catheter in the artery, can be used to compute, with high confidence, those regions of each B-scan that correspond to blood, soft plaque, dense calcium, stent struts, and adventitia. This information can be used to generate a model of the anatomy of the vessel allowing detailed information about dimensions and locations of stents to be determined automatically and with high confidence.

In one or more aspects, the present disclosure allows important questions about the position, dimension, and/or contours of vessel anatomy to be confidently and automatically answered. As a result, diagnosis can be performed using cleaner, clearer images, selective display of certain information, and alternate visualizations. The present disclosure benefits pre-treatment planning and post-treatment assessment by allowing high confidence and faster analysis of the anatomy by automating plaque/calcium detection, border detection, shoulder detection, minimum lumen area computation, stent parameter selection, stent location selection, apposition checking, restenosis detection, etc.

In one or more aspects, the present disclosure provides for improved efficiency in pre-treatment planning and post-treatment assessment and increased accuracy in diagnosis and analysis of blood vessel anatomy. As a result, vessels that actually need to be stented (e.g., to prevent over-stenting and under-stenting) can be accurately identified, increasing patient safety and treatment efficacy. For physicians, the present disclosure provides for faster workflows and automated analysis with better segmentation of blood and tissue, which can facilitate better diagnosis and post-treatment assessment. Faster workflows can also improve economic efficiency and increase patient safety, as the patient is exposed to less radiation during angiographic/fluoroscopic imaging.

Figure 1:
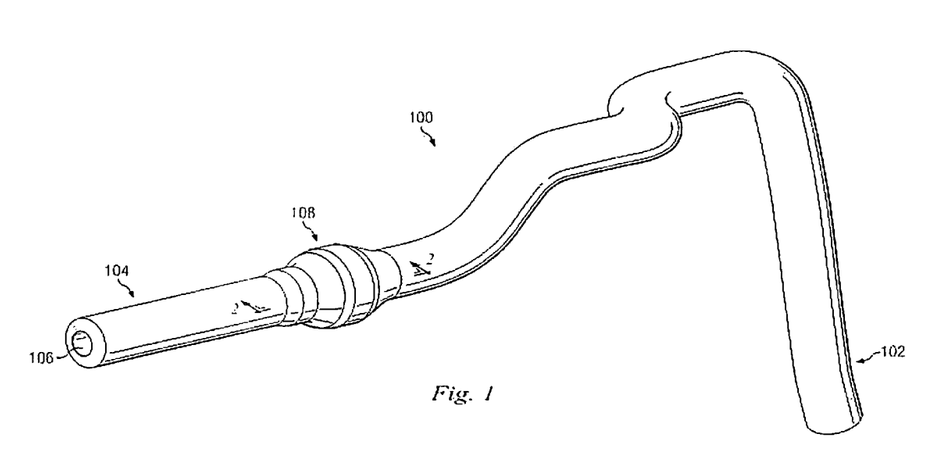
FIG. 1 is a diagrammatic perspective view of a vessel having a stenosis according to an embodiment of the present disclosure.
Figure 2:
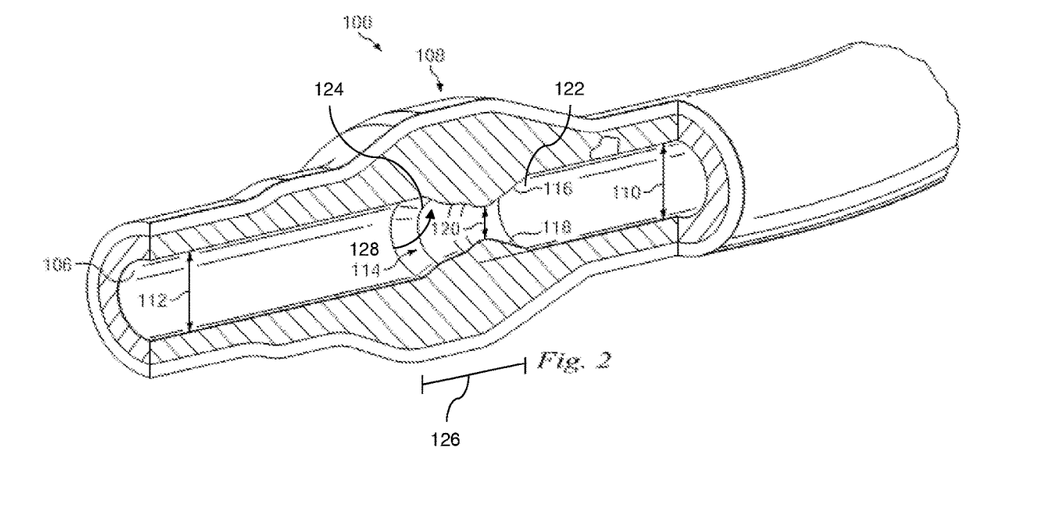
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis, according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 allows flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. The stenosis 108 can longitudinally extend between a proximal shoulder 122 and a distal shoulder 124. The shoulders 122, 124 can be areas where the plaque buildup 114 begins/ends. A length 126 of the stenosis 108 can be defined by the length between the proximal shoulder 122 and the distal shoulder 124. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Treatment of the stenosis 108 can include the positioning of a stent within the lumen 106. The stent can be configured to reestablish a normal or near-normal flow of fluid through the lumen 106 by increasing the size or cross-sectional area of the lumen 106. That is, the stent can be increase the height 120 at the narrowest point between the upper and lower portions 116, 118 to be greater than that shown in FIG. 2. A diameter of the stent can be approximately equal to the diameters 110 or 112. The stent can extend between the proximal shoulder 122 and the distal shoulder 124. A length of the stent can be similar to the length 126 of the stenosis. The proximal and distal ends of the stent can include stent struts that are well apposed to a lumen wall 128 when the stent is properly positioned within the lumen 106. The stent struts can be positioned near the proximal shoulder 122 and the distal shoulder 124.

Figure 3A:
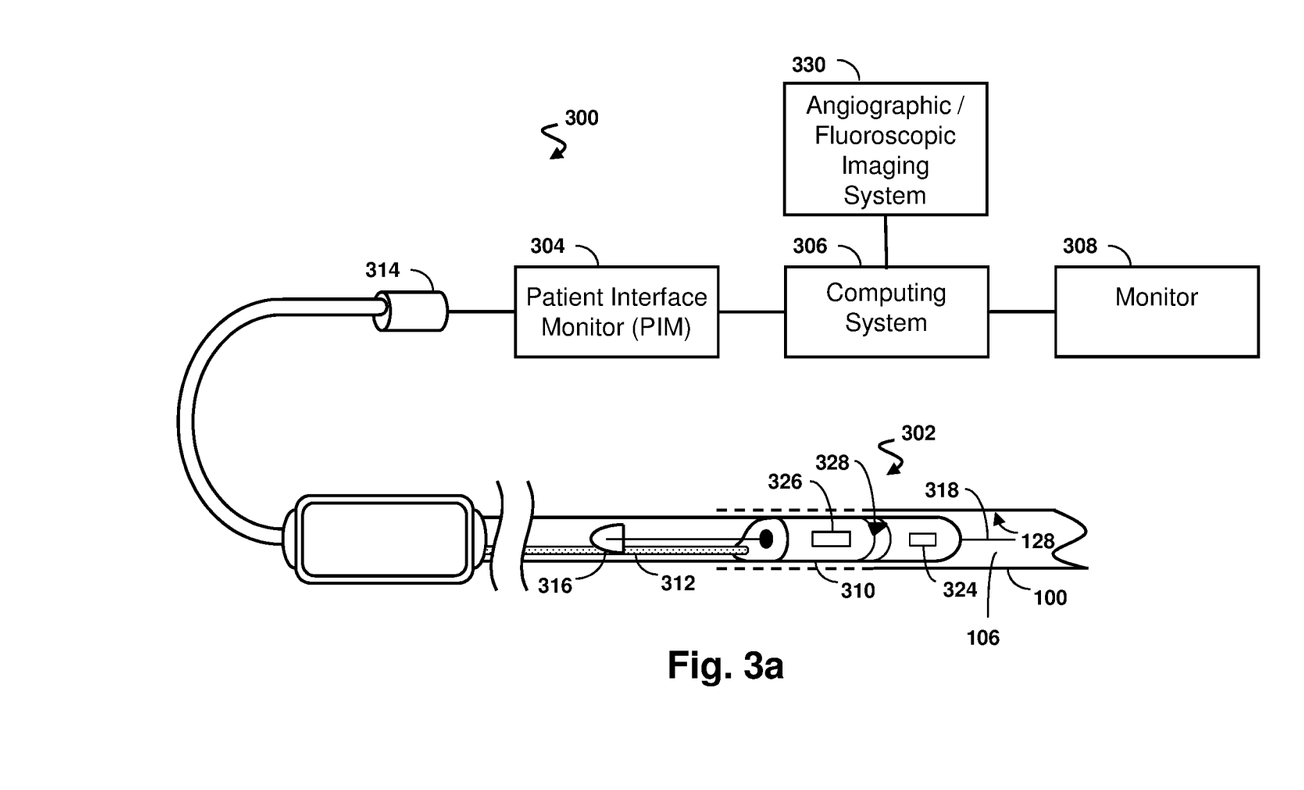
FIG. 3a is a diagrammatic schematic view of an imaging system according to aspects of the present disclosure.
Figure 3B:
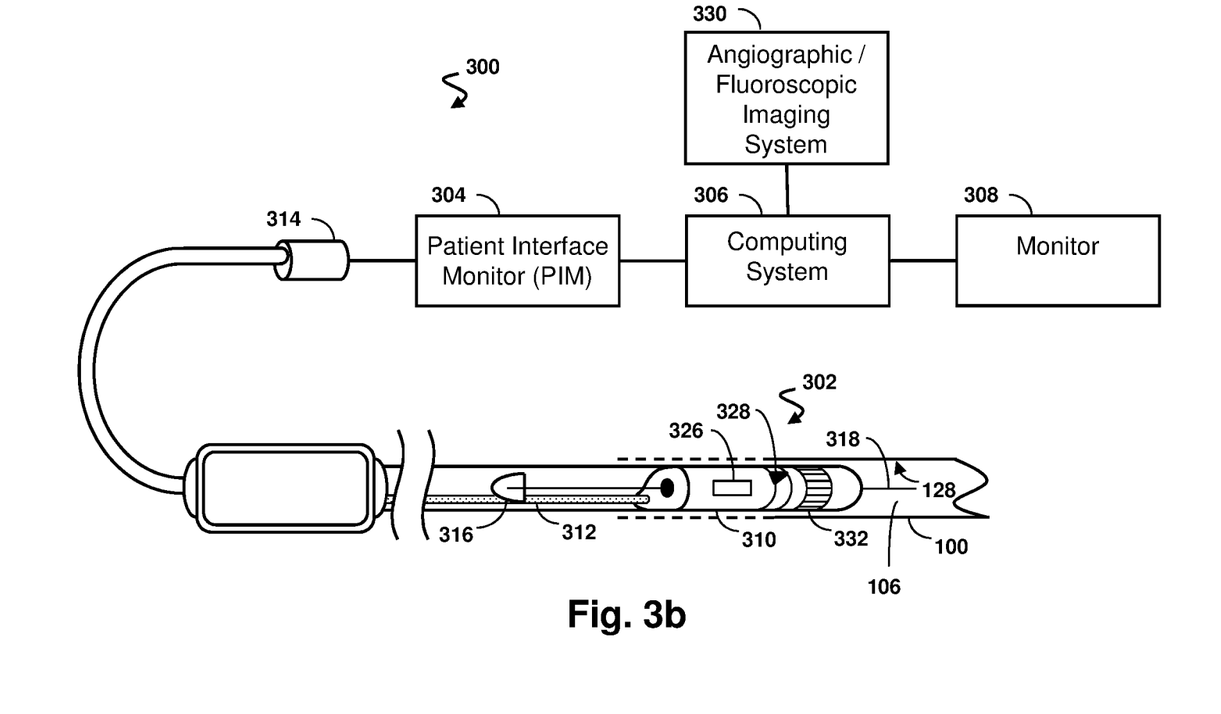
FIG. 3b is a diagrammatic schematic view of an imaging system according to aspects of the present disclosure.

FIGS. 3a and 3b are diagrammatic schematic views of an imaging system 300 according to aspects of the present disclosure. The imaging system 300 can be used in a diagnosis/pre-treatment procedure determine a proper treatment plan for deploying the stent within the vessel 100, including determining a proper length and/or diameter of the stent. The imaging system 300 can also be used in a post-stenting/post-treatment procedure verify the deployment of the stent within the vessel 100, including determining whether the stent struts are well apposed to the lumen wall 128. The imaging system 300 can include an intravascular device such as a catheter, guide wire, or guide catheter, a patient interface module (PIM) 304, an angiographic/fluoroscopic imaging system 330, a computing system 306, and a monitor 308.

At a high level, the intravascular device 302 can be a rotational IVUS device (FIG. 3a) or a solid-state IVUS device (FIG. 3b). In that regard, the intravascular device 302 can emit ultrasonic energy from the transducer element(s) included in scanner assembly 310 mounted near a distal end of the IVUS device 302. The rotational IVUS device can include one transducer element 324. The solid-state IVUS device can include an array of transducer elements 332. The array of transducer elements 332 can be positioned in an annular configuration about a longitudinal axis of the IVUS device 302. The emitted ultrasonic energy is reflected by tissue structures in the medium surrounding the scanner assembly 310, and the ultrasound echo signals are received by the transducer element(s). The transducer element(s) can be positioned adjacent a distal portion of the intravascular device 302 in some instances. In that regard, the transducer element(s) can be positioned less than 30 cm, less than 10 cm, less than 5 cm, less than 3 cm, less than 2 cm, and/or less than 1 cm from a distal tip of the IVUS device 302 in some instances. It is understood that the transducer element(s) can be positioned at any position along the intravascular device 302, including any distance from the distal tip. In some instances, the transducer element(s) can be positioned at the distal tip of the IVUS device 302. While FIGS. 3a and 3b do not show the stenosis 108 of FIGS. 1 and 2, it is understood that the intravascular device 302 can be, e.g., positioned distal to the stenosis 108 in the vessel 100 and pulled back manually or in an automated manner to image the plaque buildup 114.

The scanner assembly 310 can include integrated circuit controller chips(s) 326 configured to activate transmitter circuitry to generate an electrical pulse to excite the transducer element(s) and to accept amplified echo signals received from the transducer element(s) via amplifiers included on the integrated circuit controller chip(s) 326. In embodiments in which the intravascular device 302 includes the transducer array 332 (FIG. 3b), the integrated circuit controller chips(s) 326 can be configured to select the particular transducer array element(s) to be used for transmit and receive. The processing architecture of the integrated circuit controller chips(s) 326 can be similar to the one described in U.S. Provisional Application No. 61/746,804, filed Dec. 28, 2012, the entirety of which is hereby incorporated by reference. The frequency of the transmit signal from the transducer element(s) can be controlled by the integrated circuit controller chips 326, the PIM 304, and/or the computing system 306.

The integrated circuit controller chips(s) 326 can be configured to excite the transducer element(s) to emit ultrasonic energy with multiple frequencies at each A-scan. The transducer element(s) can be configured to emit the various frequencies to optimize the information gathered about components within the vessel 100, such as blood, plaque, adventitia, calcium, stent struts, etc. The various frequencies can interrogate respective components of the vessel 100 with improved accuracy. For example, a low-frequency A-scan can be used to detect high-density objects (e.g., stents, calcium) at low-gain reception and plaque/adventitia at high-gain reception. Low-frequency A-scans can be in the range of about 5 MHz to about 30 Mhz, about 5 Mhz to about 25 Mhz, about 10 Mhz to about 30 Mhz, and/or other suitable values. For example, a high-frequency A-scan can detect fine detail in the tissue areas. High-frequency A-scans can be in the range of about 30 Mhz to about 80 Mhz, about 30 Mhz to about 70 Mhz, about 40 Mhz to about 80 Mhz, and/or other suitable values. Low-gain reception can be can be 10 dB to 40 dB lower than the high-gain reception, depending on the system's dynamic range. While two frequency ranges—a high-frequency range and a low-frequency range—and two gain ranges—high-gain reception and low-gain reception—are described herein, it is understood that any number of frequency ranges and/or gain ranges can be utilized. The multi-frequency IVUS data can be combined to identify more clearly the different components of the vessel 100 as described in, for example, U.S. Provisional Patent Application No. 61/740,822, filed Dec. 21, 2012, the entirety of which is hereby incorporated by reference herein.

The intravascular device 302 can be configured to detect blood flow within the vessel 100. For example, the integrated circuit controller chip(s) 326 can be configured to control the transducer element(s) to emit ultrasonic energy with the same frequency for the same A-scan in a non-consecutive manner. For example, successive emissions with the same frequency (e.g., different samples of the same A-scan) can be separated in time. In that time, blood would have moved across the transducer element(s), while stationary tissue would not have. Thus, by separating ultrasonic firings for the transducer element(s) in time, blood can be identified where the IVUS data indicates movement and tissue can be identified where there is no movement. The samples can be separated by a period in the range of about 60 μs to about 150 μs, 70 μsec to about 135 μs, 80 μs to about 120 μs, and/or other suitable values. The sample period can be selected based on, e.g., the blood flow rate. The change in the IVUS data over the period between firings can be analyzed to determine if the change is suggestive of blood flow within a wedge of the field of view associated with the A-scan. If the difference in the samples is more than the expected noise or interference, then the IVUS data can be representative of blood flow. Blood flow information can be extracted as described in, for example, U.S. patent application Ser. No. 13/974,757, filed Aug. 23, 2013, the entirety of which is hereby incorporated by reference herein.

The IVUS data collected using multiple frequencies and firings separated in time can be combined to generate a more accurate model of vessel anatomy. For example, blood can be identified as areas that have little or no signal reception at low frequency A-scans. Stents and calcium can be identified as those areas that have reasonable signal strength at low-gain reception of low-frequency A-Scans. Tissue regions can be imaged using high-frequency A-scans, but a model of the vessel anatomy can include information from all exposures (e.g., low frequency with high gain, low frequency with low gain, high frequency, etc.) to generate a more accurate data representation or visual representation of the tissue and reduce blood and/or tissue speckle. While the integrated circuit controller chip(s) 326 are described as controlling the multi-frequency and time-separated emissions of the transducer element(s), in various embodiments one or more other components of the imaging system 300 (e.g., within the IVUS device 302, within the PIM 304, within the computing system 306, at another suitable location within another IVUS component, and/or a combination thereof) can perform this and/or other related steps. For example, the computing system 306 can include a signal processing card configured to control the transducer element(s) pulsing at different frequencies and at different times.

The imaging system 300 includes the PIM 304 that facilitates communication of signals between the computing system 306 and the scanner assembly 310 included in the IVUS device 302. This communication can include, among others, the steps of: (1) providing commands to the integrated circuit controller chip(s) 326, (2) providing the transmit trigger signals to the integrated circuit controller chip(s) 326 to activate the transmitter circuitry to generate an electrical pulse to excite transducer element(s), and (3) accepting amplified echo signals received from the transducer element(s) via amplifiers included on the integrated circuit controller chip(s) 326. In some embodiments, the PIM 304 performs preliminary processing of the echo data prior to relaying the data to the computing system 306. In examples of such embodiments, the PIM 304 performs amplification, filtering, and/or aggregating of the data. In an embodiment, the PIM 304 also supplies high- and low-voltage DC power to support operation of the IVUS device 302 including circuitry within the scanner assembly 310. The PIM 304 transfers the received echo signals to the computing system 306 where, among other things, the ultrasound image can be reconstructed and displayed on the monitor 308.

The computing system 306 can receive the echo data from the scanner assembly 310 by way of the PIM 304 and process the data to reconstruct an image of the tissue structures in the medium surrounding the scanner assembly 310. The echo data can used to generate a mixed-mode IVUS image including both B-scan and flow information. The B-scan image represents the two-dimensional anatomical structure of the tissue in a plane perpendicular to the longitudinal axis of IVUS device 302, with brightness at any point of the image representing of the strength of the echo signal received from the corresponding location within the tissue. Flow data is associated with a visual representation of movement of elements in the medium surrounding the scanner such as blood flow. B-mode data (e.g., using the multi-frequency ultrasonic emissions) and flow data (e.g., using ultrasonic emission separated in time) can be collected, processed, and/or combined as described herein. The computing system 306 can also output the mixed mode image on the monitor 308. The computing system 306 can be in communication with the intravascular device 302 and the angiographic/fluoroscopic imaging system 300.

The computing system 306 can be generally representative of any device suitable for performing the processing and analysis techniques discussed within the present disclosure. In some embodiments, the computing system 306 includes a processor, random access memory, and a storage medium. In that regard, in some particular instances the computing system 306 is programmed to execute steps associated with the data acquisition and analysis described herein. Accordingly, it is understood that any steps related to data acquisition, data processing, instrument control, and/or other processing or control aspects of the present disclosure may be implemented by the computing system using corresponding instructions stored on or in a non-transitory computer readable medium accessible by the computing system. In some instances, the computing system 306 is a console device. In some particular instances, the computing system 306 is similar to the s5™ Imaging System or the s5i™ Imaging System, each available from Volcano Corporation. In some instances, the computing system 306 is portable (e.g., handheld, on a rolling cart, etc.). Further, it is understood that in some instances the computing device 306 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

The imaging system 300 includes the angiographic/fluoroscopic imaging system 330 that is configured to generate a two-dimensional representation of the vessel 100. The angiographic/fluoroscopic imaging system 330 can include an x-ray source. For example, a reference image of the vessel 100 can be generated by the angiographic/fluoroscopic imaging system 330 with a radiopaque contrast agent injected into the vessel 100. Angiographic/fluoroscopic image data can be received at the computing system 306. For example, the computing system 306 can include a video capture card. The angiographic/fluoroscopic image data can be output to the monitor 308. The angiographic/fluoroscopic image data can be combined with the IVUS data to generate a high accuracy model of the vessel 100. In some embodiments, the IVUS data and the angiographic/fluoroscopic image data can be simultaneously collected (e.g., during automated or manual pullback of the IVUS device 302). In such embodiments, the IVUS data and the angiographic/fluoroscopic image data can be co-registered as described in, for example, U.S. patent application Ser. No. 13/632,916, filed Oct. 1, 2012 published as U.S. Patent Application Publication No. 2013/0030295 on Jan. 31, 2013; and/or U.S. patent application Ser. No. 13/228,229, filed Sep. 8, 2011 published as U.S. Patent Application Publication No. 2012/0004537 on Jan. 5, 2012, the entireties of which are incorporated by reference. That is, an IVUS image can be correlated to a location of the intravascular device 302 within the vessel 100 using the angiographic/fluoroscopic image data. The computing device 306 can be configured to carry out the processing steps associated with co-registering with the IVUS data and the angiographic/fluoroscopic image data.

In some embodiments, the intravascular device 302 can include one or more orientation markers 328. In some embodiments, the intravascular device 302 can include a plurality of orientation markers 328. The orientation markers 328 can be made of a radiopaque material such that orientation markers 328 are visible in the angiographic/fluoroscopic image data. The orientation markers 328 can be used to determine a longitudinal position of the intravascular device 302 along the vessel 100 in the angiographic/fluoroscopic image data. The orientation markers 328 used to determine an orientation, rotational position, and/or angular rotation of the intravascular device about its own longitudinal axis. Thus, the cross-section of the vessel 100 being imaged can be determined using the orientation markers 328 as described herein. In some embodiments, the intravascular device 302 can include three orientation markers 328 that are equally spaced apart around the circumference of the IVUS device 302. For example, the three orientation markers 328 can be spaced about 120° apart around the circumference of the IVUS device 302. In such embodiments, at least one of the three orientation markers 328 is visible in any angiographic/fluoroscopic image data. In some embodiments, the orientation markers 328 themselves can be made of the radiopaque material. In some embodiments, a band around the circumference of the intravascular device 302 can be made of a radiopaque material. The orientation markers can be notches or cutouts of the radiopaque band. The orientation markers 328 can be positioned proximal to (as shown in FIGS. 3a and 3b) or distal to the transducer element(s) on the IVUS device 302.

The orientation markers 328 can be non-symmetrically shaped, such as a sawtooth shape shown in FIGS. 3a and 3b. The sawtooth shape can include one side that extends parallel to a longitudinal axis of the intravascular device 302 and one side that extends obliquely with respect to the longitudinal axis. As the intravascular device 302 is rotated in the direction towards the top in FIGS. 3a and 3b, the angled side will appear towards the top in angiographic/fluoroscopic image data. Similarly, as the intravascular device 302 is rotated in the direction towards the bottom in FIGS. 3a and 3b, the angled side will appear towards the bottom. The computing system 306 can thus determine whether the IVUS device is rotated towards the front of the vessel 100 (e.g., the side shown in FIGS. 3a and 3b) or the back. The computing system 306 can measure the distance from the top or bottom of the intravascular device 302 to the parallel side of the orientation maker 328 to determine the angle at which intravascular device 302 is rotated. Whether the intravascular device 302 is rotated towards the front or back and the rotational angle can be used to determine a cross-section of the vessel 100 or the wedge of the total field of view of the intravascular device 302 being imaged. The sawtooth shape is a non-limiting example, and different shapes can be used in different embodiments.

A co-registered IVUS image can be rotated based on the rotational angle of the intravascular device 302 determined using the orientation marker 328. A width or diameter of the lumen 106 can be measured in the angiographic/fluoroscopic image data. The width or diameter of the lumen 106 in the co-registered IVUS image is expected to the same. The measured width can provide a starting point for determining a position and contours of the lumen wall 128 in the co-registered IVUS image. For example, the computing system 306 can be configured to use this information to carry out a border detection algorithm. The border detection algorithm is likely to provide a more accurate result when a seed point, such as the measured width or diameter from the angiographic/fluoroscopic image data, is used, as opposed to when the border detection algorithm must first guess a starting point and then follow the border. Thus, the knowledge of the cross-section of the vessel 100 being imaged by the IVUS device 302, coupled with knowledge of the position of the intravascular device 302 within the vessel 100, can be used to make a high accuracy determination of the diameter and cross-sectional area of the vessel 100.

In some embodiments, the intravascular device 302 includes some features similar to traditional rotational IVUS catheters (FIG. 3*a*), such as the Revolution® catheter available from Volcano Corporation. In some embodiments, the IVUS device includes some features similar to traditional solid-state IVUS catheters (FIG. 3*b*), such as the EagleEye® catheter available from Volcano Corporation and those disclosed in U.S. Pat. No. 7,846,101 hereby incorporated by reference in its entirety. For example, the intravascular device 302 includes the scanner assembly 310 near a distal end of the IVUS device 302 and a transmission line bundle 312 extending along the longitudinal body of the IVUS device 302. The transmission line bundle 312 terminates in a PIM connector 314 at a proximal end of the device 302. The PIM connector 314 electrically couples the transmission line bundle 312 to the PIM 304 and physically couples the intravascular device 302 to the PIM 304. In an embodiment, the intravascular device 302 further includes a guide wire exit port 316. Accordingly, in some instances the IVUS device is a rapid-exchange catheter. The guide wire exit port 316 allows a guide wire 318 to be inserted towards the distal end in order to direct the IVUS device 302 through the vessel 100.

In some embodiments, the intravascular device 302 is configured to image within the vessel 100 while being moved through the lumen 106. In some instances, the intravascular device 302 is configured to be moved through the lumen 106 and across the stenosis 108. Thus, IVUS data can be collected at a plurality of positions across the region of interest of the vessel 100. The region of interest can include the stenosis 108. In that regard, the intravascular device 302 is positioned distal of the stenosis 108 and moved proximally (i.e., pulled back) across the stenosis to a position proximal of the stenosis in some instances. In other instances, the intravascular device 302 is positioned proximal of the stenosis 108 and moved distally across the stenosis to a position distal of the stenosis. Movement of the IVUS device 302, either proximally or distally, is controlled manually by medical personnel (e.g., hand of a surgeon) in some embodiments. In other embodiments, movement of the IVUS device 302, either proximally or distally, is controlled automatically by a movement control device (e.g., a pullback device, such as the Trak Back® II Device available from Volcano Corporation). In that regard, the movement control device controls the movement of the intravascular device 302 at a selectable and known speed (e.g., 2.0 mm/s, 1.0 mm/s, 0.5 mm/s, 0.2 mm/s, etc.) in some instances. Movement of the IVUS device 302 through the vessel is continuous for each pullback or push through, in some instances. In other instances, the intravascular device 302 is moved step-wise through the vessel (i.e., repeatedly moved a fixed amount of distance and/or a fixed amount of time).

Figure 4:
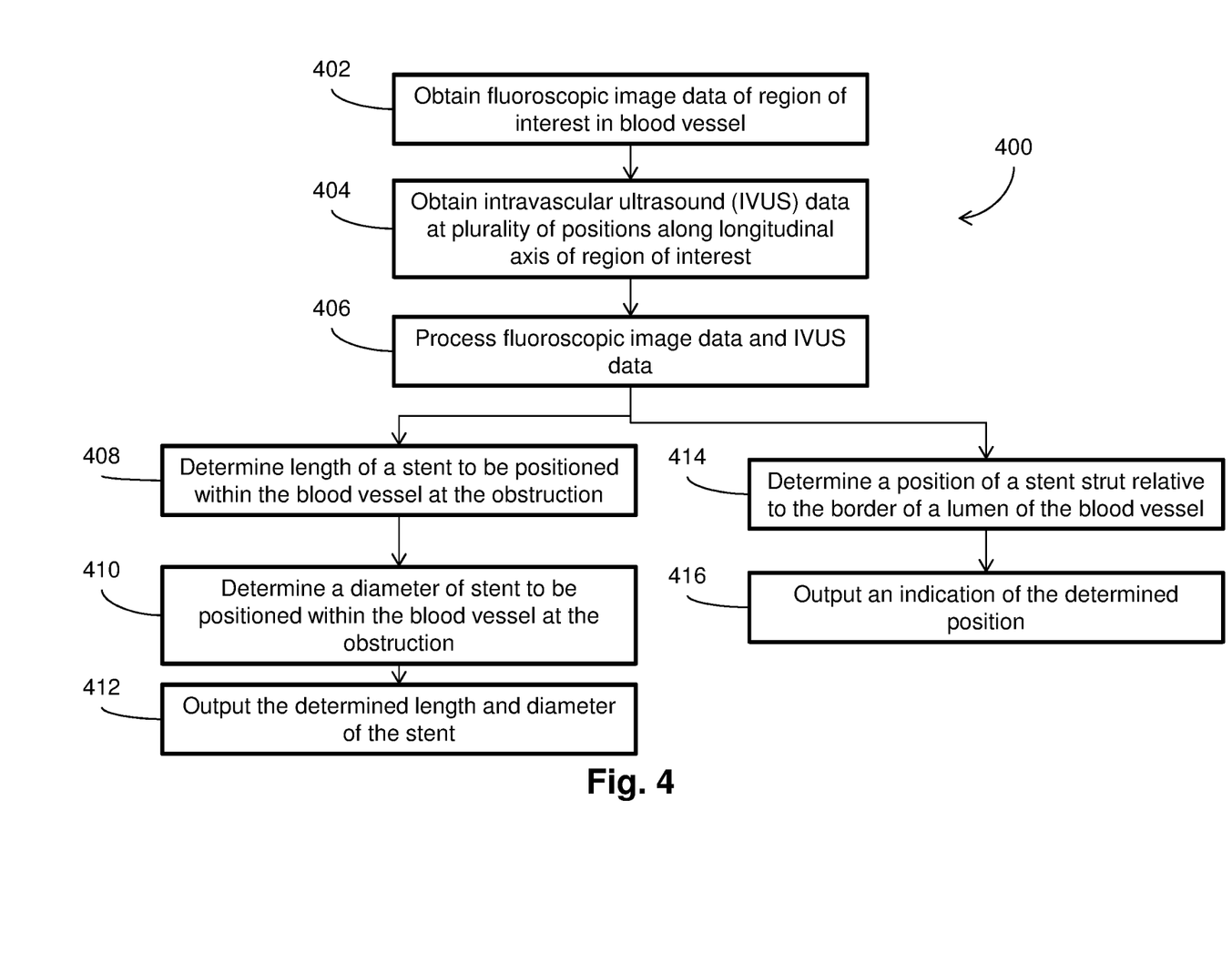
FIG. 4 is a flow diagram of a method of imaging a blood vessel according to aspects of the present disclosure.
Figure 5:
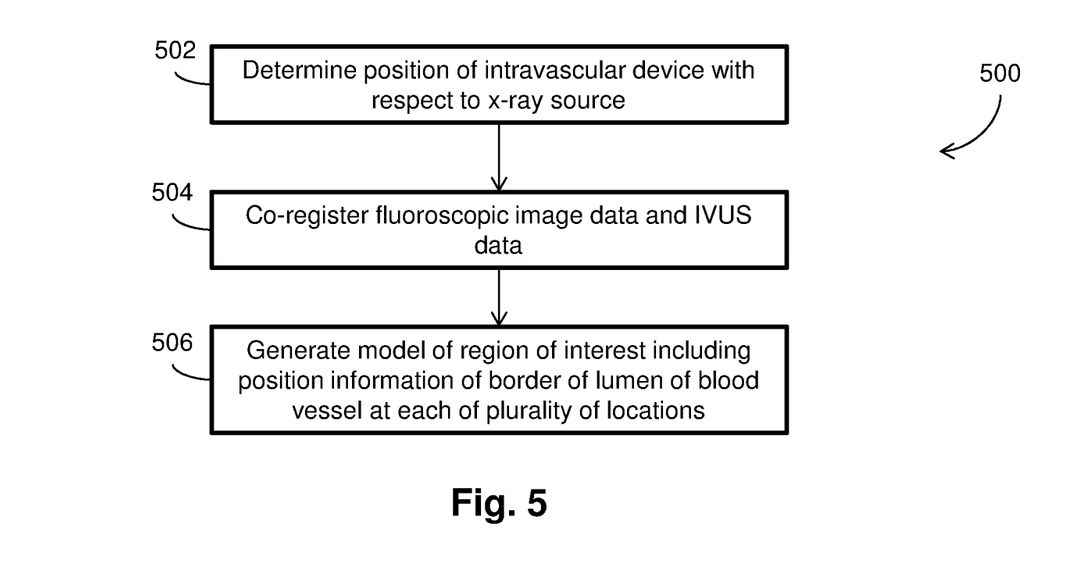
FIG. 5 is a flow diagram of a method of imaging a blood vessel according to aspects of the present disclosure.

Methods of imaging the vessel 100 are described with reference to FIGS. 4 and 5. FIGS. 4 and 5 are flow diagrams of a method 400 and 500, respectively, of imaging a blood vessel according to aspects of the present disclosure. It is understood that the steps of method 400 and/or method 500 may be performed in a different order than shown in FIGS. 4 and 5, additional steps can be provided before, during, and after the steps, and/or some of the steps described can be replaced or eliminated in other embodiments. The steps of method 400 and method 500 can be carried out within the IVUS device 302, the angiographic/fluoroscopic imaging system 330, within the PIM 304, within the computing system 306, at another suitable location within the imaging system 300, and/or a combination thereof.

The method 400 can include, at step 402, obtaining fluoroscopic image data of a region of interest in a blood vessel. The fluoroscopic image data can be acquired using an x-ray source. The method 400 can include, at step 404, obtaining IVUS data at a plurality of positions across the region of interest. The IVUS data can be acquired using an IVUS component, such as the transducer element 324 or the transducer array 332, disposed on the intravascular device 302. The region of interest can include an obstruction, such as the stenosis 108, that limits blood flow through the vessel 100. In some embodiments, the method 400 can include generating, based on the IVUS data, an IVUS image at each of the plurality of positions across the region of interest and outputting the IVUS images to the monitor 308 separate from the visual representation of a model of the region of interest (as described, for example, with respect to step 506 of method 500).

The IVUS data at each of the plurality of positions can include a plurality of components corresponding to different frequencies of ultrasound emissions. In some embodiments, the plurality of components can include a first component corresponding to a first frequency of ultrasound emissions, a second component corresponding to a second frequency with a first gain value, and a third component corresponding to the second frequency with a second gain value. While three components are described herein, it is understood that more than three components, corresponding to different frequencies and/or gain values, can be utilized. For example, the first frequency can be a relatively higher frequency, while the second frequency can be a relatively lower frequency. For example, the first gain value can be a relatively higher gain value, while the second gain value can be a relatively lower gain value. The first and second frequencies can be selected such that the ultrasound emissions behave differently in blood and in tissue. For example, the low frequency can be selected such that the wavelength of the ultrasound emission is larger than a blood cell. This can be beneficial in generating an improved accuracy model of vessel anatomy because soft plaque and blood behave similarly when interrogated by ultrasonic energy. By choosing a low frequency emission, only tissue, and not blood, is imaged by the low frequency emission. The high frequency and low frequency emissions can be used to acquire information about the tissue. In a similar manner, the high gain and low gain values can be selected to optimize acquisition of IVUS data. For example, low frequency, low gain emissions can be used to identify stent struts and calcium, both of which appear as saturated portions in the IVUS image. The IVUS data associated with the low frequency, low gain emissions can be used to more easily identify stent location such that, e.g., how well the stent is apposed to the lumen wall 128 can be readily determined.

Successive ultrasound emissions respectively associated with each of the different frequencies can be separated in time. For example, the transducer element(s) of the intravascular device 302 can be controlled to transmit ultrasonic energy in the following order: an ultrasound emission associated with the first frequency, an ultrasound emission associated with the second frequency with the first gain value, and an ultrasound emission associated with the second frequency with second gain value. While three ultrasound emissions are described herein, it is understood that more than three ultrasound emissions, e.g., associated with different frequencies and/or gain values, can be utilized. This can improve the efficiency of IVUS data collection by interleaving the emissions with different frequencies and/or gain values. For example, successive high frequency firings can be compared to extract blood flow information. The time between high frequency firings can include low frequency firing(s) to extract information about the position of tissue and/or stents. The particular order disclosed herein is a non-limiting example, and other ultrasound emission algorithms can be implemented in different embodiments.

In some embodiments, the fluoroscopic image data can be acquired before the IVUS data is acquired. For example, a reference fluoroscopic image using a contrast media can be acquired before IVUS data is acquired. The reference image can be used, for example, to generally identify the region of interest. The computing system 306 can generate a visual representation of the fluoroscopic image data and output the visual representation to the monitor 308 separate from the visual representation of a model of the region of interest (as described, for example, with respect to step 506 of method 500). The fluoroscopic image data can also be acquired simultaneously as the IVUS data is acquired. For example, fluoroscopic image data can be acquired while the IVUS data is acquired during a manual or automated pullback across the region of interest. As described herein, the fluoroscopic image data and the IVUS data can be co-registered.

The method 400 can include, at step 406, processing the fluoroscopic image data and the IVUS data. One or more sub-steps associated with processing the fluoroscopic image data and the IVUS data can be described with reference to the method 500 (FIG. 5). The method 500 can include, at step 502, determining, using the fluoroscopic image data, a position of the intravascular device 302 with respect to the x-ray source at each of the plurality of positions across the region of interest. For example, the orientation marker 328 disposed on the intravascular device 302 can be identified in the fluoroscopic image data. The computing system 306 can be configured to compute a position of the intravascular device 302 based on a position of the orientation marker 328 relative to the lumen border 128 in the fluoroscopic image data. The position can be of the intravascular device 302 along the vessel 100 and/or a rotational position of the intravascular device 302 within the vessel 100.

The method 500 can include, at step 504, co-registering the fluoroscopic image data and the IVUS data. The simultaneously-acquired fluoroscopic image data and the IVUS data can be co-registered such the location of a particular IVUS image frame along the vessel 100 can be identified in the fluoroscopic image data. The IVUS image frame can be appropriately rotated based on the determined position of the intravascular device 302 (step 502) such that the position of lumen wall 128 and the diameter of lumen 106 can be determined with improved accuracy.

The method 500 can include, at step 506, generating a model of the region of interest. The model can be generated using, for example, the determined position of the intravascular device 302 (step 502), the co-registered fluoroscopic image data and the IVUS image data (steps 402, 404, and 504), etc. The model of the region of interest can be a data representation or visual representation of one or more components of the vessel 100. The model can include position information of the lumen border or wall 128 at each of the plurality of locations across the region of interest. The model can additionally include position information of one or more components of the vessel 100 such as blood, plaque, adventitia, calcium, and stent struts. For example, the model can include a plurality of points within the vessel 100 and/or around the lumen wall 128. The points can be representative of the position and/or contours of one or more components the vessel 100. The model can additional include characterization data associated with each of the plurality of points. The characterization data can identify the components of the vessel 100. The data representation of the model can be used by the computing system 306 to automatically make pre-treatment or post-treatment determinations, including the proper length and diameter of a stent, the proper positioning of a stent strut relative to the lumen wall 128 (e.g., as described with respect to steps 408-416 herein).

In some embodiments, generating the model of the region of interest can include determining the boundary between blood and tissue within the blood vessel. The blood-tissue boundary can be determined using IVUS image data representative of blood changing randomly from frame-to-frame and/or acquired using ultrasound emissions having a different frequencies and/or gain values that cause blood to be less visible. The boundary determination can additionally consider measurements from the co-registered fluoroscopic image data. Thus, the method 500 can include computing measurements, such as the diameter, length, area, etc. of the vessel lumen. The boundary determination can additionally consider a calculated rotational position of the intravascular device relative to the x-ray source as indicated by the catheter-orienting markers visible in the fluoroscopic image data. The method 500 can include outputting an indication of the determined position of the blood-tissue boundary.

In some embodiments, generating the model of the region can include determining the boundary between vessel media and surrounding adventitia. The media-adventitia boundary can be determined based on the determined position of the boundary of blood and tissue of the blood vessel. The boundary determination can additionally consider IVUS image data. In particular, the IVUS image data associated with ultrasound emissions having a frequency that penetrates the vessel lumen (e.g., such that the media and adventitia are interrogated) can be used to determine the boundary. The boundary determination can also consider a determined position of a stent strut relative to the border of a lumen. The method 500 can include outputting an indication of the determined position of the media-adventitia boundary.

The visual representation of the model can include IVUS images, fluoroscopic images, and/or a combination thereof, that are output to the monitor 308. The visual representation can be two-dimensional or three-dimensional when viewed on the monitor 308. The visual representation can include the improved accuracy position and borders of one or more components of the vessel 100 as described herein. The one or more components of the vessel 100 can be variously colored to improve clarity (e.g., the blood can be colored differently from the tissue, the plaque can be colored differently than the tissue, etc.). The visual representation can present the co-registered fluoroscopic image data and the IVUS data in an interactive manner. For example, selecting a position along the region of interest of the vessel 100 in the fluoroscopic image can bring up the corresponding IVUS image frame. The IVUS image frames of the model can be rotated based on the position of the intravascular device 302 (step 502).

In some embodiments, the visualization can include generating a composite IVUS image using the IVUS image data associated with different frequencies and/or different gain values. The composite IVUS image can be relatively clearer with respect to the position of blood, plaque, adventitia, calcium, stent struts, etc. than the IVUS images generated using a single frequency and/or gain value. The composite IVUS image can be generated by computing the features of each pixel in an IVUS image frame, on a pixel-by-pixel basis. The features and/or content of each pixel can be based on the IVUS image data associated with different frequencies and/or different gain values. The features of each pixel can include numerical value(s) associated with echoes from the reflected ultrasound waves, whether the pixel corresponds to blood and/or tissue, what particular type of tissue the pixel corresponds to, etc. A composite pixel value can be produced by combining the information from the IVUS image data associated with different frequencies and different gain values. Combining the information in this manner can advantageously provide an optimal pixel value to filter out noise, emphasize anatomical structure, and thereby aid physicians in image interpretation. In some embodiments, the composite IVUS image can include an overlay having color indications of determined positions of a blood-tissue boundary, a media-adventitia boundary, and/or stent strut locations. The method 500 can include outputting the composite IVUS image.

In some embodiments, the visualization can include generating a longitudinal representation of the region of interest. The longitudinal representation can be a longitudinal cross section of the blood vessel at any angle, similar to the image longitudinal display (ILD) described in U.S. patent application Ser. No. 14/038,106, filed Sep. 26, 2013, the entirety of which is herein incorporated by reference. The longitudinal representation can be generated using the IVUS image data associated with different frequencies and different gain values, and/or the composite IVUS images. The method 500 can including outputting the longitudinal representation. In some embodiments, the longitudinal representation can include an overlay having color indications of determined positions of a blood-tissue boundary, a media-adventitia boundary, and/or stent strut locations. In some embodiments, the method 500 can include determining a position of minimal lumen area in the blood vessel. The minimal lumen area can occur where a stenosis causes the most narrowing of the blood vessel. The position of the minimal lumen area can be calculated based on the blood-tissue boundary. The longitudinal representation can include an indication of the position of minimal lumen area. In some embodiments, the method 500 can include providing an indication, on the longitudinal representation, of a region of stenosis proximate to the minimal lumen area. In some embodiments, the method 500 can include determining a position of the blood vessel that is un-stenosed and closest to the region of stenosis. An area or diameter of the blood vessel at the determined position can be calculated. A suggested stent diameter and length can also be calculated based on the calculated area or diameter of the blood vessel at the determined position. The suggested stent diameter and length can expand the region of stenosis to have a diameter similar to the diameter of the blood vessel proximal and distal of the region of stenosis. The method 500 can include outputting the suggested stent diameter and length.

In some embodiments, the visualization can include vector overlays on a tomographic image and/or image longitudinal display (ILD) of the lumen and vessel borders. The ILD can illustrate a longitudinal cross section of the blood vessel. The vectors overlays can include curves indicating the computed position of the borders. The computed position of the shoulders can be indicated with a graphical marker, such as tick mark(s), the ILD and/or the tomographic image.

As described herein, the IVUS images and/or fluoroscopic image data can be displayed separately from the model of the region of interest. In some embodiments, the IVUS images and/or fluoroscopic image data can be displayed at a different time than the model of the region of interest (e.g., before the model of region of interest is generated). In some embodiments, the IVUS images and/or fluoroscopic image data output to a different portion of the monitor 308 as the model of the region of interest. For example, the IVUS images and/or fluoroscopic image data can be positioned proximate to the model of the region of interest.

Referring again to FIG. 4, the method 400 can include pre-treatment planning steps 408-412 and/or post-treatment assessment steps 414-416 that are automatically performed by the computing system 306 using the generated model of the region of interest (step 506). In some embodiments, the pre-treatment planning and post-treatment assessment can be carried out in a one-touch manner. For example, a determined length and diameter of the stent (step 412) or the determined position of the stent struts relative to the lumen wall (step 416) can be output in response to a user input received at the computing system 306, without human interpretation of the IVUS data and/or the fluoroscopic image data. With respect to pre-treatment planning, the method 400 can include, at step 408, determining a length of a stent to be positioned with the blood vessel at the obstruction. The length of the stent can be determined by identifying IVUS image frames including the proximal shoulder 122 and the distal shoulder 124 (e.g., the length 126). The identified IVUS image frames can correspond to particular locations along the vessel 100 in the co-registered fluoroscopic image data. A distance between the proximal shoulder 122 and the distal shoulder 124 can be computed using the IVUS image frames and/or the fluoroscopic image data. The length of the stent can be determined to be substantially similar to the distance between the proximal shoulder 122 and the distal shoulder 124. In various embodiments, different computational methods can be carried out using the generated model of the region of interest to determine the length of the stent.

The method 400, at step 410, can include determining a diameter of a stent to be positioned within the blood vessel at the obstruction. The diameter of the stent can be computed by a width of the lumen 106 at the proximal shoulder 122 and/or the distal shoulder 126. That is, the position of the lumen wall 128 can be identified in the IVUS image frame including the proximal shoulder 122 and/or the distal shoulder 124. The model of the region of interest can identify the position of the lumen wall 128 with improved accuracy by using, e.g., the IVUS image frame rotated based on the position of the intravascular device 302 and the co-registered fluoroscopic image data. The width of the lumen 106 at the proximal shoulder 122 and/or the distal shoulder 124 can be determined to be the diameter of the stent. In various embodiments, different computational methods can be carried out using the generated model of the region of interest to determine the diameter of the stent.

The method 400 can include, at step 412, can include outputting the determined length and diameter of the stent. For example, a visual representation of the length and diameter can be output to the monitor 308. The length and diameter can be output when the generated model of the region of interest is output to the monitor 308. In some embodiments, the visual representation can include the values of the length and diameter. In some embodiments, the visual representation can include a simulated stent having the determined length and diameter positioned within the vessel 100 in the IVUS image frames and/or the fluoroscopic image data.

With respect to post-treatment assessment, the method 400 can include, at step 414, determining a position of a stent strut relative to the border of a lumen of the blood vessel. The stent struts can be readily identified in the IVUS image frame using the multi-frequency ultrasonic emissions described herein. Similarly, the position of the lumen wall 126 can be identified in the IVUS image frames including the stent struts. The model of the region of interest can identify the position of the lumen wall 128 with improved accuracy by using, e.g., the IVUS image frame rotated based on the position of the intravascular device 302 and the co-registered fluoroscopic image data. The computing system 306 can determine if the stent struts are well apposed to the lumen wall 128. For example, the computing device 306 can evaluate the spacing between the stent struts and the lumen wall 128 in the IVUS image frames. The computing system 306 also determine if the stent struts are mal-apposed such that there is too much space between the stent struts and the lumen wall 128. The vessel 100 can be at risk for restenosis when the stent is incorrectly positioned within the lumen 106.

The method 400 can include, at step 416, outputting an indication of the determined positioning of the stent struts relative to the lumen wall 128. For example, a visual representation of the indication can be output to the monitor 308. The indication can be output when the generated model of the region of interest is output to the monitor 308. The indication can be a textual or graphic. In some embodiments, the indication can be provided alongside the IVUS image frames and/or the fluoroscopic image data.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

While the present disclosure is directed primarily to ultrasonic imaging, the devices, systems, and methods disclosed herein are well suited to any type of intravascular data. For example, while IVUS imaging is described herein, it is understood that optical coherence tomography (OCT) can be utilized. One skilled in the art will recognize the application of the principles herein across other disciplines.

What is claimed is:

1. A system, comprising:
an intravascular ultrasound (IVUS) imaging catheter configured to acquire IVUS image data of a blood vessel of a patient;
a processor in communication with the IVUS imaging catheter and configured to:
receive the IVUS image data from the IVUS imaging catheter, wherein the IVUS image data is associated with different frequencies of ultrasound emissions;
determine, using the IVUS image data, a plurality of structural characteristics of tissue forming a wall of the blood vessel, wherein determining the plurality of structural characteristics includes distinguishing different types of structural characteristics from one another using the different frequencies of ultrasound emissions;
generate a visual representation of the blood vessel based on determining the plurality of structural characteristics; and
output the visual representation to a monitor in communication with the processor,
wherein the IVUS imaging catheter is configured to separate different exposures of ultrasound emissions in time by transmitting:
at a first time, an ultrasound emission associated with a first frequency;
at a second time, an ultrasound emission associated with a second frequency with a first gain value; and
at a third time, an ultrasound emission associated with the second frequency with a second gain value.

2. The system of claim 1, wherein the blood vessel is a peripheral blood vessel.

3. The system of claim 1, wherein the processor is further configured to reduce speckle in the IVUS image data by combining information from the different exposures.

4. The system of claim 3, wherein the visual representation is based on the IVUS image data with reduced speckle.

5. The system of claim 1, wherein the visual representation comprises color indications of determined positions of at least one of a blood-tissue boundary, a media-adventitia boundary, or stent strut locations.

6. The system of claim 5, wherein the visual representation comprises a cross-sectional representation of the blood vessel.

7. The system of claim 5, wherein the visual representation comprises a longitudinal representation of the blood vessel.

8. The system of claim 7, wherein the longitudinal representation of the blood vessel comprises an indication of a position of minimal lumen area in the blood vessel, wherein the position of the minimal lumen area is calculated based on the blood-tissue boundary.

9. The system of claim 8, wherein the longitudinal representation of the blood vessel comprises an indication of a position of the blood vessel that is un-stenosed and closest to the position of the minimal lumen area.

10. The system of claim 5, wherein the processor is further configured to verify a deployment of a stent within the blood vessel, including determining whether struts of the stent are apposed to the blood-tissue boundary of the blood vessel.

11. The system of claim 10, wherein the visual representation further comprises an indication of positions of the struts of the stent within the blood vessel.

12. A system, comprising:
an intravascular ultrasound (IVUS) imaging catheter configured to acquire IVUS image data of a blood vessel of a patient
a processor in communication with the IVUS imaging catheter and configured to:
receive the IVUS image data from the IVUS imaging catheter, wherein the IVUS image data is associated with different frequencies of ultrasound emissions;
determine, using the IVUS image data, a plurality of structural characteristics of tissue forming a wall of the blood vessel, wherein determining the plurality of structural characteristics includes distinguishing different types of structural characteristics from one another using the different frequencies of ultrasound emissions;
generate a visual representation of the blood vessel based on determining the plurality of structural characteristics; and
output the visual representation to a monitor in communication with the processor,
wherein the visual representation comprises color indications of determined positions of at least one of a blood-tissue boundary, a media-adventitia boundary, or stent strut locations,
wherein the visual representation comprises a longitudinal representation of the blood vessel
wherein the longitudinal representation of the blood vessel comprises an indication of a position of minimal lumen area in the blood vessel,
wherein the position of the minimal lumen area is calculated based on the blood-tissue boundary.

13. The system of claim 12, wherein the blood vessel is a peripheral blood vessel.

14. The system of claim 12, wherein the IVUS imaging catheter is configured to separate different exposures of ultrasound emissions in time by transmitting:
at a first time, an ultrasound emission associated with a first frequency;
at a second time, an ultrasound emission associated with a second frequency with a first gain value; and
at a third time, an ultrasound emission associated with the second frequency with a second gain value.

15. The system of claim 14, wherein the processor is further configured to reduce speckle in the IVUS image data by combining information from the different exposures.

16. The system of claim 15, wherein the visual representation is based on the IVUS image data with reduced speckle.

17. The system of claim 12, wherein the visual representation comprises a cross-sectional representation of the blood vessel.

18. The system of claim 12, wherein the longitudinal representation of the blood vessel comprises an indication of a position of the blood vessel that is un-stenosed and closest to the position of the minimal lumen area.

19. The system of claim 12, wherein the processor is further configured to verify a deployment of a stent within the blood vessel, including determining whether struts of the stent are apposed to the blood-tissue boundary of the blood vessel.

20. The system of claim 19, wherein the visual representation further comprises an indication of positions of the struts of the stent within the blood vessel.

21. A system, comprising:
an intravascular ultrasound (IVUS) imaging catheter configured to acquire IVUS image data of a blood vessel of a patient
a processor in communication with the IVUS imaging catheter and configured to:
receive the IVUS image data from the IVUS imaging catheter, wherein the IVUS image data is associated with different frequencies of ultrasound emissions;
determine, using the IVUS image data, a plurality of structural characteristics of tissue forming a wall of the blood vessel, wherein determining the plurality of structural characteristics includes distinguishing different types of structural characteristics from one another using the different frequencies of ultrasound emissions;
generate a visual representation of the blood vessel based on determining the plurality of structural characteristics; and
output the visual representation to a monitor in communication with the processor,
wherein the visual representation comprises color indications of determined positions of at least one of a blood-tissue boundary, a media-adventitia boundary, or stent strut locations,
wherein the processor is further configured to verify a deployment of a stent within the blood vessel, including determining whether struts of the stent are apposed to the blood-tissue boundary of the blood vessel.

22. The system of claim 21, wherein the blood vessel is a peripheral blood vessel.

23. The system of claim 21, wherein the IVUS imaging catheter is configured to separate different exposures of ultrasound emissions in time by transmitting:
at a first time, an ultrasound emission associated with a first frequency;
at a second time, an ultrasound emission associated with a second frequency with a first gain value; and
at a third time, an ultrasound emission associated with the second frequency with a second gain value.

24. The system of claim 23, wherein the processor is further configured to reduce speckle in the IVUS image data by combining information from the different exposures.

25. The system of claim 24, wherein the visual representation is based on the IVUS image data with reduced speckle.

26. The system of claim 21, wherein the visual representation comprises a cross-sectional representation of the blood vessel.

27. The system of claim 21, wherein the visual representation comprises a longitudinal representation of the blood vessel.

28. The system of claim 27, wherein the longitudinal representation of the blood vessel comprises an indication of a position of minimal lumen area in the blood vessel, wherein the position of the minimal lumen area is calculated based on the blood-tissue boundary.

29. The system of claim 28, wherein the longitudinal representation of the blood vessel comprises an indication of a position of the blood vessel that is un-stenosed and closest to the position of the minimal lumen area.

30. The system of claim 21, wherein the visual representation further comprises an indication of positions of the struts of the stent within the blood vessel.

* * * * *